United States Patent [19]

Minami et al.

[11] 3,962,443

[45] June 8, 1976

[54] ANTIBACTERIAL PHARMACEUTICAL COMPOSITIONS AND PROCESSES FOR PREPARATION THEREOF

[75] Inventors: Shinsaku Minami, Yamato-Kouriyama; Jun-ichi Matsumoto, Takatsuki; Kazuyo Kawaguchi, Nara; Shinsaku Mishio, Osaka; Masanao Shimizu, Kobe; Yoshiyuki Takase, Amagasaki; Shinichi Nakamura, Takatsuki, all of Japan

[73] Assignee: Dainippon Pharmaceutical Co., Ltd., Osaka, Japan

[22] Filed: Feb. 21, 1975

[21] Appl. No.: 551,923

Related U.S. Application Data

[62] Division of Ser. No. 386,626, Aug. 8, 1973, Pat. No. 3,887,557.

[30] Foreign Application Priority Data

| Aug. 14, 1974 | Japan | 47-81288 |
| Dec. 19, 1972 | Japan | 47-128022 |
| Dec. 22, 1972 | Japan | 48-269 |
| Dec. 26, 1972 | Japan | 48-3108 |
| Dec. 27, 1972 | Japan | 48-570 |
| May 25, 1973 | Japan | 48-58909 |
| June 19, 1973 | Japan | 48-69651 |

[52] U.S. Cl. .................................. 424/251
[51] Int. Cl.² .............................. A61K 31/505
[58] Field of Search .................................. 424/251

[56] References Cited
UNITED STATES PATENTS

| 3,320,257 | 5/1967 | Lesher | 260/254.4 F |
| 3,725,405 | 4/1973 | Santilli et al. | 260/254.4 F |
| 3,753,993 | 8/1973 | Lesher et al. | 260/287 |
| 3,770,742 | 11/1973 | Matsumoto et al. | 260/254.4 F |

*Primary Examiner*—Frederick E. Waddell
*Attorney, Agent, or Firm*—Sherman & Shalloway

[57] ABSTRACT

This invention provides compounds of the following formula

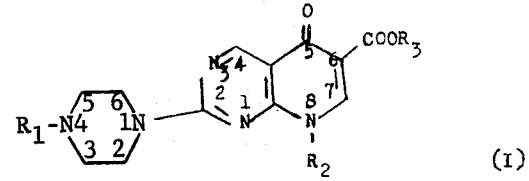

wherein $R_1$ is a hydrogen atom, an alkyl group having 1 to 4 carbon atoms, a hydroxyalkyl group having 2 to 4 carbon atoms, a benzyl group, a benzyl group subsituted by methoxy, a phenyl group, a propargyl group or an acyl group; $R_2$ is hydrogen atom, an alkyl group having 1 to 4 carbon atoms, an alkyl group having 2 to 4 carbon atoms substituted by hydroxy or halogen, a vinyl group, an allyl group, or a benzyl group $R_3$ is a hydrogen atom or an alkyl group having 1 to 6 carbon atoms;
and salts thereof, and processes for preparing them. Some of the compounds have antibacterial activities.

3 Claims, No Drawings

ANTIBACTERIAL PHARMACEUTICAL COMPOSITIONS AND PROCESSES FOR PREPARATION THEREOF

This is a division of application Ser. No. 386,626, filed Aug. 8, 1973, now U.S. Pat. No. 3,887,557.

This invention relates to new and useful piperazine derivatives having antibacterial activities, intermediates thereof, processes for preparing them, and also to their use.

This invention provides compounds of the following formula

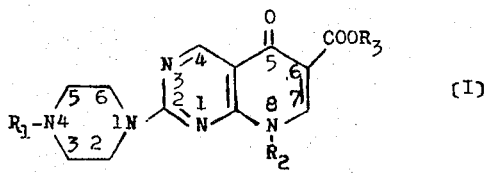

[I]

wherein $R_1$ is a hydrogen atom, an alkyl group having 1 to 4 carbon atoms, a hydroxyalkyl group having 2 to 4 carbon atoms, a benzyl group, a benzyl group substituted by methoxy, a phenyl group, a propargyl group or an acyl group; $R_2$ is a hydrogen atom, an alkyl group having 1 to 4 carbon atoms, an alkyl group having 2 to 4 carbon atoms substituted by hydroxy or halogen, a vinyl group, an allyl group, or a benzyl group $R_3$ is a hydrogen atom or an alkyl group having 1 to 6 carbon atoms;
and salts thereof.

The term "acyl group," as used in the present specification and appended claims, denotes a carbonic or carboxylic acid residue such as a lower alkanoyl group such as formyl, acetyl, trifluoroacetyl, or propionyl, a lower alkoxycarbonyl group such as methoxycarbonyl or ethoxycarbonyl, and a phenyl-substituted lower alkoxycarbonyl group, e.g. benzyloxycarbonyl.

In the present specification and appended claims, the term "lower alkyl group" either in itself or as part of other groups denotes an alkyl group containing 1 to 4 carbon atoms.

Of the compounds of formula [I] the following compounds and salts thereof are suitable as antibacterial agents.

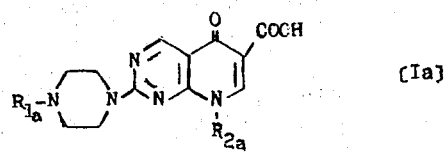

[Ia]

In this formula $R_{1a}$ is a hydrogen atom, an alkyl group having 1 to 4 carbon atoms, a hydroxyalkyl group having 2 to 4 carbon atoms, a phenyl group or a propargyl group; and $R_{2a}$ is an alkyl group having 1 to 4 carbon atoms, an alkyl group having 2 to 4 carbon atoms substituted by hydroxy or halogen, a vinyl group, an allyl group, or a benzyl group.

Especially suitable compounds of this invention as antibacterial agents are shown below.

5,8-Dihydro-8-ethyl-2-(1-piperazinyl)-5-oxopyrido[2,3-d]pyrimidine-6-carboxylic acid,
5,8-dihydro-8-ethyl-2-(4-ethyl-1-piperazinyl)-5-oxopyrido[2,3-d]pyrimidine-6-carboxylic acid,
8-benzyl-5,8-dihydro-2-(1-piperazinyl)-5-oxopyrido[2,3-d]pyrimidine-6-carboxylic acid,
5,8-dihydro-2-(1-piperazinyl)-8-vinyl-5-oxopyrido[2,3-d]pyrimidine-6-carboxylic acid,
8-(2-chloroethyl)-5,8-dihydro-2-(1-piperazinyl)-5-oxopyrido[2,3-d]pyrimidine-6-carboxylic acid, and
pharmaceutically acceptable acid addition salts or alkali metal salts of these compounds.

The above-described compounds of this invention are sometimes obtained as hydrates and they are also within the scope of this invention. In the present specification, these hydrates will be described as coming within the scope of the compounds of formula [I] in the free form, other than the salts of the compounds of formula [I].

Relatively similar compounds to the compounds of this invention are disclosed in British patent specification No. 1,129,358 (published Oct. 2, 1968) and German Offenlegungschrift No. 2,143,369 (published Mar. 9, 1972) as antibacterial agents.

We have made an attempt to prepare antibacterial agents which are more useful than these known compounds, and found that by introducing a piperazine into the 2-position of the pyrido[2,3-d]pyrimidine nucleus, there can be obtained compounds having characteristic antibacterial activity (especially, against Pseudomonas aeruginosa or Mycobacterium tuberculosis).

The compounds of formula [I] are synthesized by any of the following processes 1 to 7.

Process 1

The compounds of formula [I] are prepared by reacting compounds (a) of the following formula

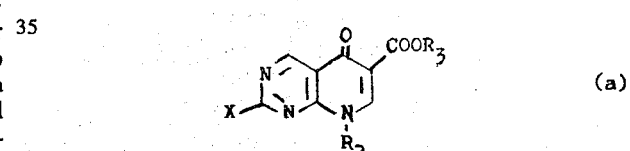

(a)

wherein X is a halogen atom, a lower alkylthio group, a lower alkoxy group, and $R_2$ and $R_3$ are the same as defined above;
with compounds (b) of the following formula

(b)

wherein $R_1$ is the same as defined above.

The reaction in this process 1 is performed by heating the compounds (a) and (b) at atmospheric pressure in a solvent, if desired, in the presence of a base such as sodium bicarbonate or triethylamine to give the compounds of formula [I] in good yield.

Where compounds (a) in which X is a halogen atom are used as starting material, it is preferred to perform the reaction in the presence of a base, as a dehydrohalogenating agent, such as sodium bicarbonate, sodium carbonate, potassium carbonate, or triethylamine. Usually, the compounds (a) and (b) are used in stoichiometric amounts. Furthermore, the compounds (b) may be used in excess to make them serve also as a dehydrohalogenating agent. The compounds (b) may be used in the form of hydrate or acid addition salts of, for example, hydrochloric acid. The preferred reaction temperature is in the range of 60°C. to 120°C.

The solvent used in this reaction should be selected according to the properties of the materials to be used. Examples of the solvent are alcohols such as ethanol or propanol, aromatic hydrocarbons such as benzene or toluene, halogenoalkanes such as dichloroethane or chloroform, ethers such as tetrahydrofuran, dioxane or diphenyl ether, acetonitrile, dimethyl sulfoxide, dimethylformamide, and water. They may be used either alone or in mixture.

Process 2

Of the compounds of formula [I], the following compounds

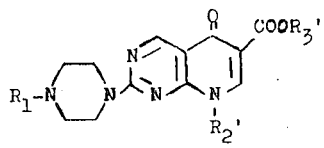

wherein $R_2'$ is an alkyl group having 1 to 4 carbon atoms, an alkyl group having 2 to 4 carbon atoms substituted by halogen, an allyl group or a benzyl group and $R_3'$ is an alkyl group having 1 to 6 carbon atoms, and $R_1$ is the same as defined above, can be obtained by heating compounds of formula (c) below

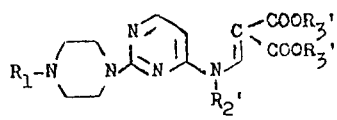

wherein $R_1$, $R_2'$ and $R_3'$ are the same as defined above, to induce intramolecular cyclization.

The reaction in process 2 is performed by heating the compounds (c) directly or in a high-boiling solvent, such as diphenyl ether, o-dichlorobenzene, diphenylene oxide, dibutyl phthalate, or mixtures of these. The suitable heating temperature is 140° to 260°C.

It is also possible to perform the cyclization reaction in the presence of a conventional cyclization agent such as polyphosphoric acid, a polyphosphoric acid alkyl ester, concentrated sulfuric acid or phosphorus pentoxide. Where polyphosphoric acid, polyphosphoric acid alkyl ester or phosphorus pentoxide is used as the cyclization agent, the reaction is generally carried out in a solvent such as benzene, dioxane or dimethylformamide. When concentrated sulfuric acid is used, the reaction is generally carried out in a solvent such as acetic anhydride or acetic acid. Of course, depending upon the properties of the cyclization agent, it can be made to serve also as the solvent. If the cyclization agent is used, the reaction is carried out at relatively low temperatures.

Process 3

Of the compounds of formula [I], those of the following formula

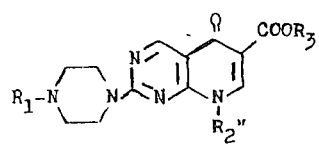

wherein $R_1$ and $R_3$ are the same as defined above, and $R_2''$ is an alkyl group having 1 to 4 carbon atoms, an alkyl group having 2 to 4 carbon atoms substituted by hydroxy or halogen an allyl or a benzyl group; are obtained by reacting compounds (d) (the compound of formula (I) in which $R_2$ is a hydrogen atom),

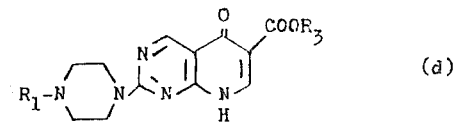

wherein $R_1$ and $R_3$ are the same as defined above, with an alkylating agent corresponding to $R_2''$.

Known alkylating agents can be used. Specific examples include alkyl halides such as methyl iodide, ethyl iodide, allyl bromide, benzyl chloride, 1,2-dibromoethane, ethylene chlorohydrin or ethylene bromohydrin, and lower alkyl esters such as dimethyl sulfate, diethyl sulfate, methyl p-toluenesulfonate, or triethyl phosphate.

The reaction in the process 3 is generally carried out by reacting the compound (d) with a stoichiometric amount of the alkylating agent in an inert solvent at an elevated temperature. If desired, the alkylating agent may be used in excess. The solvent may be either nonaqueous or hydrous. Examples of the solvent are ethanol, dioxane, dimethylformamide, dimethyl sulfoxide and water. The reaction is promoted by adding an acid acceptor, for example, a base such as an alkali carbonate, an alkali hydroxide, an alkali metal alkoxide, sodium hydride, triethylamine, or benzyltrimethyl ammonium hydroxide. Where the alkylating agent is made to act in a hydrous solvent, the carboxylic acid ester portion sometimes undergoes hydrolysis depending upon the reaction conditions, and thus is converted to a free carboxylic acid. Furthermore, when compounds of formula (d) in which $R_1$ is a hydrogen atom are alkylated, N-alkylated products at the 4-position of the piperazine nucleus can be obtained together with N-alkylated products at the 8-position of the pyrido[2,3-d]pyrimidine nucleus. Accordingly, the desired products can be obtained by suitably choosing the starting material, solvent and alkylating agent.

Where the product of the formula [I-b] is a compound in which $R_2''$ is a hydroxyalkyl group, it may be further halogenated with a halogenating agent such as thionyl chloride or phosphorus oxychloride to convert the hydroxyalkyl group to a halogenoalkyl group.

Process 4

Compounds of formula [I-b] can also be obtained by heating compounds of formula (e) below

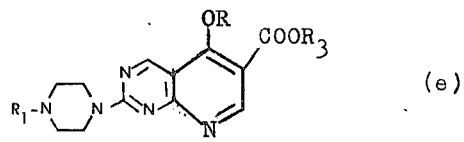

wherein R is a lower alkyl group and $R_1$ and $R_3$ are as defined above,
either directly or in the presence of an alkylating agent such as used in process 3 described above.

The reaction in process 4 is carried out by directly heating the compound (e) or in a solvent such as lower alcohols (such as methanol, ethanol, propanol or diethylene glycol), ethers (such as diethyl ether, dioxane, tetrahydrofuran, 1,2-dimethoxyethane, dimethyleneglycol dimethyl ether or diphenyl ether), or aromatic hydrocarbons (such as benzene or toluene). The reaction is promoted by adding a catalyst such as a Lewis acid (such as boron trifluoride, or aluminum chloride) or a protonic acid (such as toluenesulfonic acid, sulfuric acid, hydrochloric acid or phosphoric acid). The heating temperature is 40° to 250°C.

By reacting the compound (e) with the above-described alkylating agent in at least a stoichiometric amount in a solvent, the compound [I-b] can be obtained. Examples of the solvent are water, dimethylformamide, and dimethyl sulfoxide in addition to the above-exemplified solvents. When alkylating agents are liquid alkyl halides or alkyl phosphates, they may be used concurrently as solvents.

Process 5

Compounds of formula [I] wherein $R_3$ is a hydrogen atom, that is, compounds of formula [I-c] below

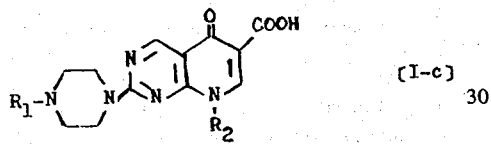

wherein $R_1$ and $R_2$ are the same as defined above, can be obtained by hydrolyzing compounds of formula [I] wherein $R_3$ is an alkyl group having 1 to 6 carbon atoms, that is, compounds of formula (h) below

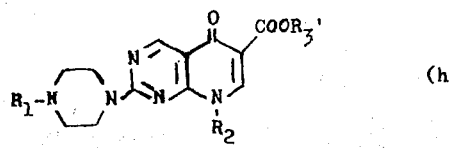

wherein $R_1$, $R_2$ and $R_3'$ are the same as defined above.

The hydrolysis reaction in the process 5 is carried out by contacting the compound (h) with water. Generally, in order to promote the reaction, it is performed in the presence of a catalyst such as an acid or base.

Examples of the acid are inorganic acids such as hydrochloric acid, hydrobromic acid, hydroiodic acid, sulfuric acid or phosphoric acid, and organic acids such as acetic acid, oxalic acid or toluenesulfonic acid.

Examples of the base are alkali metal hydroxides such as sodium hydroxide or barium hydroxide, alkali metal carbonates such as sodium carbonate or potassium carbonate, and sodium acetate.

This reaction may also be performed by directly heating the material in the presence of the above acid, and then adding water. The solvent is usually water, but depending upon the properties of the material, a hydrous solvent such as ethanol, dioxane, ethyleneglycol dimethyl ether, benzene or acetic acid may also be used. The reaction temperature may be room temperature, but usually 50° to 200°C., preferably 70° to 120°C.

Where $R_1$ in the compound (h) is a formyl or trifluoroacetyl group, $R_1$ is converted to a hydrogen atom by being hydrolyzed together with the ester portion of this compound.

Process 6

Of the compounds of formula (I), those in which $R_1$ is a hyrogen atom, that is, compounds of formula [I-d] below

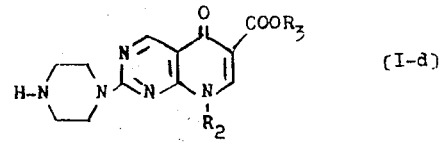

wherein $R_2$ and $R_3$ are the same as defined above, can be obtained by hydrolyzing or hydrogenolyzing compounds of formula (i) below

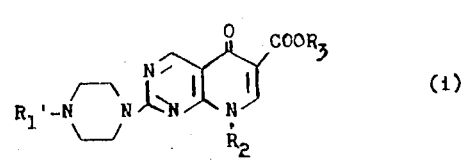

wherein $R_2$ and $R_3$ are the same as defined above, and $R_1'$ is an acyl group, an arylsulfonyl group, a benzyl group, a vinyl group, a trityl group, or a group —CH$_2$—CH$_2$—Z in which Z is a halogen atom, a lower alkoxy group, a benzyloxy group, an alcoholic hydroxy group or its derivative, or a group which may form a tertiary or quaternary amine together with the residue;
according to the nature of $R_1'$.

The acyl group as $R_1'$ means the carboxylic or carbonic acid residues as described above.

The derivatives of the alcoholic hydroxyl group as Z include, for example, acyloxy groups such as acetyloxy or ethoxycarbonyloxy; aryl sulfonyloxy groups such as tosyloxy or benzenesulfonyloxy, or lower alkylsulfonyloxy groups such as methanesulfonyloxy or ethanesulfonyloxy; or S-aryldithiocarbonyloxy groups such as S-phenyldithiocarbonyloxy, or lower alkyldithiocarbonyloxy group such as S-methyldithiocarbonyloxy or S-ethyldithiocarbonyloxy groups.

Specific examples of the group that can form a tertiary or quaternary amine together with the residue are —N(CH$_3$)$_2$, —N(C$_2$H$_5$)$_2$,

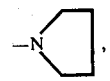

—N$^\oplus$(CH$_3$)$_3$$^\ominus$, —N$^\oplus$(C$_2$H$_5$)$_3$OH$^\ominus$, and

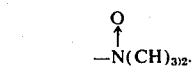

The hydrolysis reaction in the process 6 is generally carried out by reacting the compound (i) with a mineral acid or an alkali hydroxide. At this time, the ester portion is also hydrolyzed to form a free carboxylic acid. Where $R_1'$ is a formyl, trifluoroacetyl or trityl group, it is split off under mild hydrolysis conditions without affecting the other functional groups. This reaction is carried out at 20° to 150°C.

The hydrogenolysis reaction in the process 6 is carried out by hydrogenating the compound (i) using, for example, a hydrogen gas stream in a solvent in the presence of a catalyst such as platinum, palladium or Raney nickel, or by hydrogenolyzing the compound (i) with metallic sodium in liquid ammonia. The above catalytic hydrogenolysis reaction proceeds at room temperature. If desired, however, it may be carried out at an elevated temperature up to 60°C. Suitable solvents are ethyleneglycol, dioxane, dimethylformamide, ethanol, and acetic acid. Especially when $R_1'$ is a benzyl, trityl or tosyl group, such a group can be split off with metallic sodium in liquid ammonia.

Process 7

Of the compounds of formula (I), those in which $R_2$ is a vinyl group, that is, compounds of the formula (I-3) below

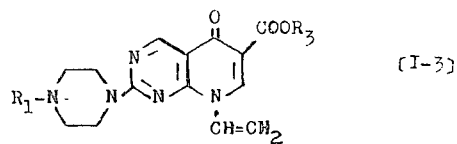

wherein $R_1$ and $R_3$ are the same as defined above, can be obtained by heating compounds (j) below

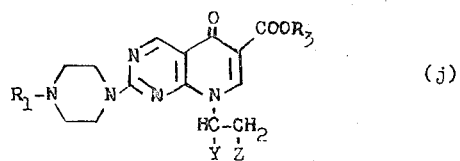

wherein $R_1$ and $R_3$ are the same as defined above; and Y and Z are different from each other, and each represent a hydrogen atom, a halogen atom, a lower alkoxy group, a benzyloxy group, an alcoholic hydroxy group or its derivative, or a group that can form a tertiary or quaternary amine together with the residue, with the proviso that either Y or Z is always a hydrogen atom.

The derivatives of the alcoholic hydroxy groups as Y and Z include, for example, acyloxy groups such as acetyloxy or ethoxycarbonyloxy; arylsulfonyloxy groups such as tosyloxy or benzenesulfonyloxy, or lower alkylsulfonyloxy groups such as methanesulfonyloxy or ethanesulfonyloxy; or S-aryldithiocarbonyloxy groups such as S-tolyldithiocarbonyloxy or S-phenyldithiocarbonyloxy, or lower alkyldithiocarbonyloxy such as S-methyldithiocarbonyloxy or S-ethyldithiocarbonyloxy groups.

Specific examples of the group as Y and Z that can form a tertiary or quaternary amine with the residue are $-N(CH_3)_2$, $-N(C_2H_5)_2$,

$-N^\oplus(CH_3)_3I^\ominus$, $-N^\oplus(C_2H_5)_3OH^\ominus$, and

The reaction in process 7 is carried out by simply heating the compound (j) or heating it in the presence of a catalyst such as an acidic substance, an acid anhydride or a base. Examples of the catalyst are ordinary acids such as hydrochloric acid, sulfuric acid, polyphosphoric acid, phosphoric anhydride, formic acid, acetic acid, toluenesulfonic acid, or potassium bicarbonate, Lewis acids such as thionyl chloride, phosphorus oxychloride, boron trifluoride or zinc chloride, alkali hydroxides, alkali carbonates, metal hydrides such as sodium hydride, alkali metal alkoxide such as sodium ethylate, sodium methoxide or potassium tert.-butoxide, pyridine, collidine, benzyltrimethylammonium hydroxide, acetic anhydride, phthalic anhydride, silver oxide, iodine, and tert.-butyl lithium.

The reaction temperature is usually 50° to 270°C. The reaction proceeds in the absence of solvent, but preferably, it is carried out in a solvent. Examples of the solvents are water, alcohol, acetic acid, dimethylformamide, dimethyl sulfoxide, ether, benzene, dioxane, tetrahydrofuran, and pyridine.

In this reaction, depending upon the nature of $R_1$ and/or $R_3$ of the starting compound (j) and the reaction conditions, $R_1$ and/or $R_3$ of the final product [I-e] may sometimes be replaced with a hydrogen atom.

The starting compound (a) used in process 1 is a known compound disclosed in German Deutsche Offenlegungschrift No. 2,143,369 described above. The starting compound (b) is a known compound and can be obtained by known methods.

The starting compound (c) used in process 2 is obtained by reacting the corresponding 2-(1-Piperazinyl)-6-aminopyrimidine and alkoxymethylenemalonate in accordance with the method disclosed in British Patent Specification No. 1,129,358.

The compound (e) used in process 4 is a novel compound which is obtained by heating a compound (f) below

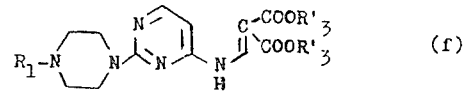

wherein $R_1$ and $R_3'$ are the same as defined above; together with an excess of a halogenating agent such as phosphorus oxychloride in a solvent such as benzene through intramolecular cyclization to produce a compound to the following formula (g) below

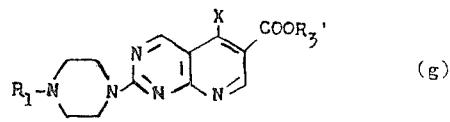

wherein $R_1$ and $R_3'$ are the same as described above, and X is a halogen atom;

and then heating this compound with an alkali metal alkoxide in a solvent such as dimethyleneglycol dimethyl ether, dioxane, benzene or a lower alcohol, or with a lower alcohol in the presence of a base such as an alkali metal tert.-butoxide or trimethylbenzylammonium hydroxide.

The starting compound (i) used in the process 6 partly covers the compound of formula [I] in accordance with this invention, and can be prepared in the same manner as in process 1 or by reacting the compound (d) with an alkylating agent in the same manner as in the process 3.

The starting material (j) used in the process 7 is a novel compound, and can be prepared by reacting the starting compound (d) used in the process 3 with a halide of the formula $$CH_2Z-CHY-halogen \quad (k)$$

wherein Y and Z are the same as defined above; in the same way as described in the process 3.

The compound (d) used as the starting compound in the process 3 and the compound (h) used as the starting compound in the process 5 are part of the compounds [I] of this invention, and can be prepared by any of the suitable methods described above.

The compounds of the present invention prepared in the above process can be isolated and purified by usual methods. The compounds [I] can be obtained in the free state or in the form of salts depending upon the selection of the starting materials and the reaction conditions. Furthermore, the compounds [I] can be converted to pharmaceutically acceptable amine salts or carboxylic acid salts by treatment with acid or alkali, or vice versa. The acid may be a variety of organic and inorganic acids, examples of which are hydrochloric acid, acetic acid, lactic acid, succinic acid, oxalic acid and methanesulfonic acid.

The antibacterial activities of the typical compounds of this invention are shown in Tables I to V together with those of the compounds disclosed in the aforesaid British Patent or German Patent.

In the Tables II to IV, the $ED_{50}$ and $ID_{50}$ values were calculated in accordance with the Behrens-Kaerber method [Arch. Exp. Path. Pharm., 162, 480 (1931)]. The compound numbers are those described in the Examples and compounds PA and AT-616 are as follows:

Compound PA:
5,8-Dihydro-8-ethyl-2-pyrrolidino-5-oxopyrido [2,3-pyrimidine-6-carboxylic acid, which is the most valuable compound disclosed in the British Patent.

Compound AT-616:
5,8-Dihydro-8-ethyl-2-(3-hydroxy-pyrrolidino)-5-oxopyrido[2,3-d)]pyrimidine-6-carboxylic acid, which is the most valuable compound disclosed in the German Patent.

Table I

1) In vitro antibacterial activity against 3 strains of bacteria

| Compound | $R_1$ | $R_2$ | $R_3$ | Staphylococcus aureus Terajima | MIC (μg/ml) Escherichia coli K-12 | Pseudomonas aeruginosa Tsuchijima |
|---|---|---|---|---|---|---|
| 1 | H | $C_2H_5$— | H | 30 | 1 | 10 |
| 2 | H | n-$C_3H_7$— | H | 100 | 3 | 30 |
| 4 | | $\underset{OH}{CH_3\overset{|}{C}HCH_2-}$ | $C_2H_5$— | H | 30 | 3 | 100 |
| 11* | H | | $C_2H_5$— | H | 30 | 3 | 10 |
| 17 | $CH_3O\text{-}\langle\text{-}\rangle\text{-}CH_2-$ | | $C_2H_5$— | H | 10 | 3 | 100 |
| 21 | $C_2H_5$— | | $C_2H_5$— | H | 30 | 1 | 100 |
| 33 | H | $\langle\text{-}\rangle\text{-}CH_2-$ | | H | 100 | 3 | 10 |
| 38 | CH≡CCH$_2$— | | $C_2H_5$— | H | 10 | 3 | >100 |
| 50 | H | | $CH_2$=CHCH$_2$— | H | 100 | 10 | 30 |
| 54* | H | | $CH_2$=CH— | H | >100 | 3 | 3 |
| 63* | H | | ClCH$_2$CH$_2$— | H | 30 | 3 | 30 |
| PA | | | | | 10 | 1 | 100 |
| AT-616 | | | | | 30 | 1 | 100 |

*hydrochloride
The minimum inhibitory concentration (MIC) was determined by the well known serial dilution method.
Experimental conditions:
Medium: nutrient broth, pH 7.0 (5 ml/tube)
Inoculum: 1 drop of 1 : $10^5$ dilution of an overnight broth culture per tube
Incubation temperature and time: 37°C for 48 hours Table II 2) In vivo efficacy against systemic infection with Pseudomonas aeruginosa in mice

| Compound No. | Route | Dose (mg/kg) 200 | 100 | 50 | 25 | 12.5 | 6.3 | 3.1 | $ED_{50}$ (mg/kg) |
|---|---|---|---|---|---|---|---|---|---|
| 1 | ip | — | — | 8/8 | 8/8 | 4/8 | 2/8 | 1/8 | 10.5 |
|   | po | 8/8 | 4/8 | 0/8 | — | — | — | — | 100 |

Table II-continued

2) In vivo efficacy against systemic infection with Pseudomonas aeruginosa in mice

| Compound No. | Route | 200 | 100 | 50 | Dose (mg/kg) 25 | 12.5 | 6.3 | 3.1 | $ED_{50}$ (mg/kg) |
|---|---|---|---|---|---|---|---|---|---|
| 2 | ip | — | — | 8/8 | — | — | — | — | 35.4 |
|   | po | 5/8 | — | — | — | — | — | — | <200 |
| 11* | ip | — | — | — | 8/8 | — | — | — | <17.7 |
|   | po | 8/8 | 7/8 | — | — | — | — | — | <100 |
| 21 | ip | — | 4/8 | 0/8 | — | — | — | — | ≈100 |
|   | po | 4/8 | — | — | — | — | — | — | ≈200 |
| 33 | ip | — | — | — | 8/8 | — | — | — | <17.7 |
| 50 | ip | — | 8/8 | 7/8 | 1/8 | — | — | — | 35 |
| 63* | ip | — | — | 8/8 | 8/8 | — | — | — | <17.7 |
| PA | ip | — | 0/8 | — | — | — | — | — | >100 |
|   | po | 0/8 | — | — | — | — | — | — | >200 |
| AT-616 | ip | — | 3/8 | — | — | — | — | — | >100 |
|   | po | 1/8 | — | — | — | — | — | — | >200 |

The numerical figures in the table show the number of the survival/the total number. 0/8 means that all of 8 mice died. 8/8 means that all 8 mice survived: The survival rate of non-treated control was 0.8.
Experimental conditions:
Organism: Pseudomonas aeruginosa No. 12
Mice: male mice (ddY-S) weighing 20 g approximately
Infection: intraperitoneal infection with 50 to 100 $LD_{50}$ of a bacterial suspension in 4% gastric mucin (about $5 \times 10^3$ cells/mouse)
Medication: twice, about 5 minutes and 6 hours after infection
Drug: an alkaline solution for parenteral administration and a suspension in 0.2% CMC for oral administration
Observation of mortality: 7 days
i.p.: intraperitoneal administration
p.o: oral administration

Table III

3) In vivo efficacy against systemic infection with Salmonella typhymurium in mice

| Compound No. | Route | 100 | 50 | Dose (mg/kg) 25 | 12.5 | 6.3 | $ED_{50}$ (mg/kg) |
|---|---|---|---|---|---|---|---|
| 1 | ip | — | — | 8/8 | 8/8 | 4/8 | 6.3 |
|   | po | — | 8/8 | 8/8 | 4/8 | 0/8 | 12.5 |
| 4 | ip | — | 8/8 | — | — | — | <35.4 |
|   | po | — | 8/8 | — | — | — | <35.4 |
| 11* | po | — | 8/8 | — | — | — | <35.4 |
| 21 | ip | — | — | 8/8 | — | — | <17.7 |
|   | po | — | — | 8/8 | — | — | <17.7 |
| 33 | ip | — | — | 7/8 | 4/8 | 1/8 | 12.5 |
| 38 | po | — | 8/8 | 6/8 | 0/8 | — | 21.0 |
| 54* | po | — | 8/8 | 6/8 | 2/8 | — | 17.7 |
| PA | ip | 9/10 | 5/10 | 3/10 | 0/10 | — | 43.5 |
|   | po | 10/10 | 4/10 | 3/10 | 0/10 | — | 46.7 |

The numerical figures in the table show the number of the survived/the total number. 0/8 means that all of 8 mice died. 8/8 means that all 8 mice survived. The survival rate of non-treated control was 0/8.
Experimental conditions.
Organism: Salmonella typhimurium S-9
Mice: male mice (ddY-S) weighing 20 g approximately
Infection: Intraperitoneal infection with 50 to 100 $LD_{50}$ of a bacterial suspension in nutrient broth (about $10^5$ cells/mouse)
Medication: twice a day for 4 days from the day of infection.
Drug: an alkaline solution for parenteral administration and suspension in 0.2% CMC for oral administration
Observation: 14 days
i.e.: intraperitoneal administration
p.o.: oral administration

Table IV

4) Antituberculous activity in vitro

| Compound | $R_1$ | $R_2$ | $R_3$ | Mycobacterium tuberculosis $H_{37}R_v$ | Kurono | $H_{37}R_v$ resistant |
|---|---|---|---|---|---|---|
| 6 | ⟨phenyl⟩ | $C_2H_5$— | H | 6.3 | 6.3 | 6.3 |
| PA |  |  |  | 100 | 100 | 100 |

*INH, PAS, SM-resistant strain
The minimum inhibitory concentration (MIC:μg/ml) was determined by the well known serial dilution method.
Experimental conditions:
Medium: Kirchner medium containing 0.2% bovine albumin, pH 7.0 (3 ml/tube)
Inoculum: 1 drop of 1:$10^2$ dilution of a culture in Modified Kirchner medium for 2 weeks (OD=0.3) per tube
Incubation temp. and time: 37°C for 3 weeks

Table V

5) Acute toxicity in mice

| Compound | Route | 4000 | Dose (mg/kg) 2000 | 1000 | 500 | $LD_{50}$ (mg/kg) |
|---|---|---|---|---|---|---|
| 1 | iv | — | — | 0/6 | 6/6 | 700 |
|   | po | 6/6 | 6/6 | — | — | >4000 |

The numerical figures in the table show the number of survival/the total number. 0/6 means that all of 6 mice died and 6/6 means that all of mice survived.

The compound was in an alkaline solution for introvenous administration and a suspension containing 0.2% CMC for oral administration, and was administered to male mice (ddY-S) weighting 20 g approximately. After 7 days, the incidence of death was recorded and $ID_{50}$ value was estimated.

i.v.: intraveneous administration,
p.o.: oral administration

A clinical dosage of the compound [I] depends on body weight, age and administration route but it is generally in the range of 100 mg – 5 g/day, preferably of 200 mg–3g/day.

The compounds [I] may be used as medicines, for example, in the form of pharmaceutical preparations containing the compound in admixture with organic or inorganic, solid or liquid pharmaceutical adjuvants suitable for peroral, parenteral, enteral or local administration. Pharmaceutically acceptable adjuvants are substances that do not react with the compounds, for example, water, gelatin, lactose, starch, cellulose, preferably microcrystalline cellulose, carboxymethyl cellulose, methyl cellulose, sorbitol, magnesium stearate, talc, vegetable oils, benzyl alcohol, gums, propylene glycol, polyalkylene glycols, methylparaben and other known medicinal adjuvants. The pharmaceutical preparations may be, for example, powders tablets, ointments, suppositories, creams or capsules, or in liquid form as solutions, suspensions or emulsions. They may be sterilized and/or contain assistants such as preserving, stabilizing, wetting or emulsifying agents, salts for regulating the osmotic pressure or buffers. They may further contain other therapeutically valuable substances. The preparations are prepared by conventional methods.

EXAMPLE A

| | |
|---|---|
| 5,8-dihydro-8-ethyl-2-(1-piperazinyl)-5-oxopyrido[2,3-d]pyrimidine-6-carboxylic acid | 250 g |
| Starch | 54 g |
| Calcium carboxymethyl cellulose | 40 g |
| Microcrystalline cellulose | 50 g |
| Magnesium stearate | 6 g |

The above components are blended, granulated and made into tablets in a conventional manner. These 1000 tablets each weighing 400 mg were formed.

EXAMPLE B

| | |
|---|---|
| 5,8-dihydro-8-ethyl-2-(1-piperazinyl)-5-oxopyrido[2,3-d]pyrimidine-6-carboxylic acid | 250 g |
| Starch | 50 g |
| Lactose | 35 g |
| Talc | 15 g |

The above components were blended and granulated and filled into 1,000 capsules in accordance with conventional methods.

EXAMPLE C

| | |
|---|---|
| 5,8-dihydro-8-ethyl-2-(1-piperazinyl)-5-oxopyrido[2,3-d]pyrimidine-6-carboxylic acid hydrochloride | 5 g |
| Sorbitol | 30 g |
| Sugar | 40 g |
| Methylparaben | Small amount |
| Sodium carboxymethyl cellulose | Small amount |
| Flavor | Small amount |
| Water to make | 100 ml |

The following Examples illustrate the preparation of the compounds of the present invention. In all of the Examples, percentages are by weight unless otherwise specified.

Examples 1 to 14 illustrate the preparation of the compounds of this invention in accordance with the process 1.

EXAMPLE 1

5,8-Dihydro-8-ethyl-2-(1-piperazinyl)-5-oxopyrido[2,3-d]pyrimidine-6-carboxylic acid
(compound 1)

A mixture containing 1.33 g of 5,8-dihydro-8-ethyl-2-methylthio-5-oxopyrido[2,3-d]pyrimidine-6-carboxylic acid, 1.94 g of piperazine hexahydrate and 20 ml. of dimethyl sulfoxide was heated at 110°C for 1 hour with stirring. The separated solid was collected by filtration, washed with ethanol, and then dried at such a temperature that did not rise above 50°C to give 1.57 g of the trihydrate of the product as nearly colorless needles, m.p. 253°–255°C.

Analysis Calcd. for $C_{14}H_7O_3N_5 \cdot 3H_2O$ : C, 47.05; H, 6.49; N, 19.62; $H_2O$, 15.12. Found: C, 46.87; H, 6.41; N, 19.54; $H_2O$, 15.1.

The trihydrate was further dried at 110°C to give 1.31 g of the anhydrous product, m.p. 253°– 255°C.

Analysis —Calcd. for $C_{14}H_{17}O_3N_5$: C, 55.43; H, 5.65; N, 23.09. Found C, 55.48; H, 5.74; N, 22.85.

EXAMPLE 2

5,8-Dihydro-8-ethyl-2-(4-methyl-1-piperazinyl)-5-oxopyrido-[2,3-d]pyrimidine-6-carboxylic acid
(compound 3)

A mixture containing 1.33 g of 5,8-dihydro-8-ethyl-2-methylthio-5-oxopyrido[2,3-d]pyrimidine-6-carboxylic acid, 1.30 g of 4-methylpiperazine, and 20 ml of dimethyl sulfoxide was heated at 110°C for 1 hour with stirring. The separated solid was collected by filtration, washed with ethanol, and recrystallized from dimethylformamide to give 1.86 g of the product, as nearly coloress needles, m.p. 232 - 233°C.

EXAMPLE 3

5,8-Dihydro-8-ethyl-2-[4-(2-hydroxy-n-propyl)-1-piperazinyl]-5-oxopyrido[2,3-d]pyrimidine-6-carboxylic acid (compound 4)

Following the procedure described in Example 2 using in place of 4-methyl piperazine 1.44 g of 4-(2-hydroxy-n-propyl)piperazine, there is obtained 1.40 g of the product, as colorless needles, m.p. 214°– 216°C.

EXAMPLE 4

5,8-Dihydro-8-ethyl-2-(4-phenyl-1-piperazinyl)-5-oxoprido[2,3-d]pyrimidine-6-carboxylic acid (compound 6).

Following the procedure described in Example 2 using in place of 4-methyl piperazine 1.62 g of 4-phenylpiperazine, there is obtained 1.50 g of the product, as yellowish orange needles, m.p. 247°–248°C.

EXAMPLE 5

2-(4-Benzyl-1-piperazinyl)-5,8-dihydro-8-ethyl-5-oxopyrido[2,3-d]-pyrimidine carboxylic acid (compound 7).

Following the procedure described in Example 2 using in place of 4-methyl piperazine 1.75 g of 4-benzylpiperazine, there is obtained 1.40 g of the product, as colorless scales, m.p. 204°– 206°C.

EXAMPLE 6

2-(4-Acetyl-1-piperazinyl)-5,8-dihydro-8-ethyl-5-oxopyrido[2,3-d]pyrimidine-6-carboxylic acid (compound 10)

Following the procedure described in Example 2 using in place of 4-methyl piperazine 1.28 g of 4-acetylpiperazine, there is obtained 1.51 g of the product, as yellowish needles, m.p. 298°–300°C.

EXAMPLE 7

The following compounds were prepared in the same way as in Example 2.

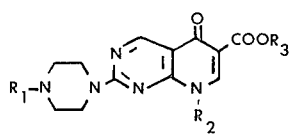

| Compound | $R_1$ | $R_2$ | $R_3$ | m.p. °C. |
|---|---|---|---|---|
| 17 | $CH_3O$-C$_6$H$_4$-$CH_2$- | $C_2H_5$— | H | 198 – 199 |
| 19 | $CH_3$— | C$_6$H$_5$-$CH_2$- | H | 251 – 255 |
| 18 | $HOCH_2CH_2$— | $C_2H_5$— | H | 266 – 228 |
| 20 | $C_2H_5OCO$— | $C_2H_5$— | H | >300 |
| 21 | $C_2H_5$— | $C_2H_5$— | H | 228 – 230 |
| 22 | $CH_3$— | $C_2H_5$— | $C_2H_5$— | 146 – 147 |
| 24 | $HCO$— | $C_2H_5$— | H | >300 |
| 52 | $CH_3$— | $CH_2$=CH— | H | 233 – 234 |
| 53 | H | $CH_2$=CHCH$_2$— | H | 253 – 255 |
| 33 | H | C$_6$H$_5$-$CH_2$- | H | 250 – 253 |
| 34 | H | $HOCH_2CH_2$— | H | 249 – 251 |
| 37 | $CH_3$ | $CH_2$=CHCH$_2$— | H | 256 – 258 |
| 38 | $CH\equiv C-CH_2$— | $C_2H_5$— | H | 254 – 257 |
| 39 | (CH$_3$O)$_3$-C$_6$H$_2$-CH$_2$ | $C_2H_5$— | H | 218 – 220 |

EXAMPLE 8

The following compounds were prepared in the same way as in Example 2.

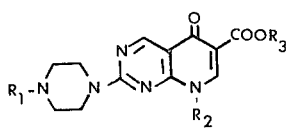

| Compound | $R_1$ | $R_2$ | $R_3$ |
|---|---|---|---|
| 64 | $C_2H_5$— | $CH_2$=CH— | H |
| 65 | C$_6$H$_5$- | $CH_2$=CH— | H |
| 66 | C$_6$H$_5$-$CH_2$- | $CH_2$=CH— | H |
| 67 | $CH_3$CHCH— $\;\;\;\;$ OH | $CH_2$=CH— | H |

EXAMPLE 9

5,8-Dihydro-2-(1-piperazinyl)-8-n-propyl-5-oxopyrido[2,3-d]pyrimidine-6-carboxylic acid (compound 2)

A mixture containing 1.40 g of 5,8-dihydro-2-methylthio-8-n-propyl-5-oxopyrido[2,3-d]pyrimidine-6-carboxylic acid, 2.94 g of piperazine hexahydrate, and 20 ml of dimethylsulfoxide was heated at 100 - 110°C for 1.5 hours. The precipitate was collected, washed with ethanol, and then recrystallized from water to yield 1.40 g of the product, as colorless needles, m.p. 259°–261°C.

EXAMPLE 10

5,8-Dihydro-2-(4-methyl-1-piperazinyl)-8-n-propyl-5-oxopyrido[2,3-d]pyrimidine-6-carboxylic acid (compound 26)

Following the procedure described in Example 9 using in place of piperazine hexahydrate a molar equivalent quantity of 4-methylpiperazine, there is obtained the product, m.p. 254°–257°C.

EXAMPLE 11

5,8-Dihydro-8-ethyl-5-oxo-2-(1-piperazinyl)-pyrido[2,-3]pyrimidine-6-carboylic acid (compound 1)

A mixture containing 1.0 g of 5,8-dihydro-8-ethyl-2-methoxy-5-oxopyrido[2,3-d]pyrimidine-6-carboxylic acid 1.6 g of piperazine hexahydrate and 50 ml of dimethyl sulfoxide was heated at 100°–110°C for 1.5 hours. After removal of dimethyl sulfoxide by distillation under reduced pressure, the residual solid was recrystallized from dimethylformamide to give 1.0 g of the product, as colorless needles, m.p. 253°–255°C.

EXAMPLE 12

5,8-Dihydro-8-(2-hydroxyethyl)-2-(4-methyl-1-piperazinyl)-5-oxopryrido[2,3-d]pyrimidine-6-carboxylic acid (compound 31)

Following the procedure described in Example 11, there is obtained the product, m.p. 232.5 –233.5.

EXAMPLE 13

Ethyl 2-(4-acetyl-1-piperazinyl)-5,8-dihydro-8-ethyl-5-oxopyrido[2,3-d]pyrimidine-6-carboxylate (compound 42)

A mixture containing 1.0 g of ethyl 2-chloro-5,8-dihydro-8-ethyl-5-oxopyrido[2,3-d]pyrimidine-6-carboxylate, 0.60 g of sodium bicarbonate, 20 ml of dimethyl sulfoxide, and 0.60 g of 1-acetylpiperazine was heated at 120°C for 1.5 hours with stirring. The dimethylsulfoxide was distilled off in vacuo and the residue was taken up in chloroform. The chloroform solution was washed with water, dried over anhydrous magnesium sulfate, and concentrated to dryness. The residual solid was recrystallized from a mixture of n-hexane and acetone to yield 1.21 of the product, m.p. 208°–210°C with decomposition.

EXAMPLE 14

5,8-Dihydro-2-(1-piperazinyl)-8-vinyl-5-oxopyrido[2,3-d]pyrimidine-6-carboxylic acid hydrochloride (compound 54)

To a mixture containing 1.2 g of piperazine hexahydrate and 6 ml. of dimethylformamide heated at 80°C was added a solution of ethyl 5,8-dihydro-2-methylthio-8-vinyl-5-oxopyrido[2,3-d]pyrimidine-6-carboxylate (0.47 g) in 6 ml of dimetylformamide. The reaction mixture was allowed to react at the same temperature for 2.5 hours with stirring. After removal of the solvent under reduced pressure 30 ml of 15% hydrochloric acid solution was added to the reaction mixture, which was then heated in a steam bath for 30 minutes. The solid that precipitated was collected, and dissolved in 30 ml of water. The resulting aqueous solution was treated with decolorizing charcoal followed by filtration. Addition of 2 ml of concentrated hydrochloric acid to the filtrate gave a solid on cooling, which was collected and recrystallized from diluted aqueous ethanol to yield 0.47 g of the product as colorless prisms, m.p. 298°–301°C with decomposition.

Examples 15 to 19 illustrate the preparation of the salts of the compounds of this invention.

EXAMPLE 15

Potassium 5,8-dihydro-8-ethyl-2-(1-piperazinyl)-5-oxopyrido[2,3-d]pyrimidine-6-carboxylate (compound 32)

To a solution of potassium carbonate (2.76 g) in 60 ml of water was added 6.06 g of 5,8-dihydro-8-ethyl-2-(1-piperazinyl)-5-oxopyrido[2,3-d]pyrimidine-6-carboxylic acid. The resulting mixture was heated on a steam bath until it became a clear solution. Ethanol was added to the solution, and the mixture was then kept below room temperature by external cooling to yield the precipitate, which was collected and washed with ethanol. There is obtained 4.2 g of the product m.p. above 300°C.

EXAMPLE 16

5,8-Dihydro-8-ethyl-2-(1-piperazinyl)-5-oxopyrido[2,3-d]pyrimidine-6-carboxylic acid hydrochloride (compound 11)

To a stirred solution of saturated alcoholic hydrochloric acid (20 ml) was added, under ice-cooling, in portions of 1.28 g of 5,8-dihydro-8-ethyl-2-(1-piperazinyl)-5-oxopyrido[2,3-d]pyrimidine-6-carboxylic acid.

The reaction mixture was then allowed to stand with continuous stirring while being maintained below 5°C.

The resulting precipitate was collected, and washed with ethanol to yield 1.40 g of the product, as colorless needles, m.p. above 300°C.

EXAMPLE 17

5,8-Dihydro-8-n-propyl-2-(1-piperazinyl)-5-oxopyrido[2,3-d]pyrimidine-6-carboxylic acid hydrochloride (compound 28)

Following the procedure described in Example 16, there is obtained the product, m.p. 294° – 295°C with decomposition.

EXAMPLE 18

5,8-Dihydro-8-ethyl-2-(1-piperazinyl)-5-oxopyrido[2,3]pyrimidine-6-carboxylic acid acetate (compound 12)

To a stirred suspension containing 0.30 g of 5,8-dihydro-8-ethyl-2-(1-piperazinyl)-5-oxopyrido[2,3-d]pyrimidine-6-carboxylic acid and 20 ml of an absolute ethanol was added 2 ml. of glacial acetic acid at room temperature. The reaction mixture was stirred for an additional two hours. The resulting precipitate was collected, and washed with ethanol to yield 0.35 g of the product, as colorless needles, m.p. 257° – 258°C.

EXAMPLE 19

The following salt were prepared in the same way as in Example 18.

5,8-Dihydro-8-ethyl-2-(1-piperazinyl)-5-oxopyrido[2,3-d]pyrimidine-6-carboxylic acid lactate (compound 13): m.p. 230° – 235°C.

5,8-Dihydro-8-ethyl-2-(1-piperazinyl)-5-oxopyrido[2,3-d]pyrimidine-6-carboxylic acid succinate (compound 14): m.p. 202° – 204°C.

5,8-Dihydro-8-ethyl-2-(1-piperazinyl)-5-oxopyrido[2,3-d]pyrimidine-6-carboxylic acid oxalate (compound 15): m.p. 261° – 263°C.

5,8-Dihydro-8-ethyl-2-(1-piperazinyl)-5-oxopyrido[2,3-d]pyrimidine-6-carboxylic acid methanesulfonate 16): m.p. 294° – 295°C. (dec.)

Examples 20 to 25 illustrate the preparation of the compounds of this invention by the process 2).

EXAMPLE 20

Ethyl 2-(4-acetyl-1-piperazinyl)-5,8-dihydro-5-oxopyrido[2,3-d]pyrimidine-6-carboxylate (compound 59)

To 16 ml of diphenyl ether heated at 250° – 255°C was added with stirring 2.0 g of diethyl, N-[2-(4-acetyl-1-piperazinyl)-4-pyrimidinyl]-aminomethylenemalonate, gentle refluxing was continuted for 10 minutes, and then the mixture allowed to cool to room temperature. To the mixture was added 12 ml of n-hexane and the resulting precipitate was collected, washed with ethanol, and recrystallized from ethanol to yield 1.52 g of the product, m.p. 300° – 302°C with decomposition.

EXAMPLE 21

The following compounds were prepared in the same way as in Example 20.

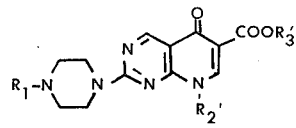

| Compound | R₁ | R₂' | R₃' | mp°C | |
|---|---|---|---|---|---|
| 42 | CH₃CO— | C₂H₅— | C₂H₅— | 208 – 210 | (dec.) |
| 56 | H | C₂H₅— | C₂H₅— | 156 – 158 | |
| 60 | CF₃CO— | C₂H₅— | C₂H₅ | 244 – 246 | |

EXAMPLE 22

Ethyl 5,8-dihydro-8-ethyl-2-(4-methyl-1-piperazinyl)-5-oxopyrido[2,3-d]pyrimidine-6-carboxylate (compound 22)

A mixture containing 1.0 g of diethyl N-ethyl-N-[2-(4-methyl-1-piperazinyl)-4-pyrimidinyl]aminomethylene malonate and 6.0 g of polyphosphoric acid was heated at 140°C for 20 minutes, and then poured into ice-water. The resulting mixture was made alkaline with 28% aqueous ammonia and extracted with chloroform. The extract was washed with water, and dried over anhydrous magnesium sulfate, and the solvent was removed by distillation to give a crude product which was recrystallized from water to give 0.72 g of the product, m.p. 146° – 147°C.

EXAMPLE 23

Ethyl 2-(4-benzyl-1-piperazinyl)-5,8-dihydro-8-ethyl-5-oxopyrido[2,3-d]pyrimidine-6-carboxylate (compound 55)

Following the procedure described in Example 22 there is obtained the product, m.p. 151° – 153°C.

EXAMPLE 24

Ethyl 5,8-dihydro-8-ethyl-2-(1-piperazinyl)-5-oxopyrido[2,3-d]pyrimidine-6-carboxylate (compound 56)

Diethyl N-ethyl-N-[2-(1-piperazinyl)-4-pyrimidinyl]-aminomethylenemalonate (1.0 g) was heated at 250°C for 30 minutes and the resulting solid was recrystallized from ethanol to give 0.73 g of the product, m.p. 156° – 158°C.

EXAMPLE 25

Ethyl 5,8-dihydro-2-(4-methyl-1-piperazinyl)-5-oxopyrido[2,3-d]pyrimidine-6-carboxylate (compound 70)

To a 50 ml of diphenyl ether heated at 210° – 220°C was added with stirring 7.0 g of diethyl N-[2-(4-methyl-1-piperazinyl)-4-pyrimidinyl]aminomethylenemalonate, and heating was continued for 1 hour. To the resulting mixture, after being cooled, was added 50 ml of n-hexane. The resulting precipitate was collected, washed with ethanol, and recrystallized from dimethylformamide to yield 6.3 g of the product, m.p. 266° – 268°C.

Examples 26 to 35 illustrate the preparation of the compounds of this invention by the process 3).

EXAMPLE 26

Ethyl 2-(4-acetyl-1-piperazinyl)-5,8-dihydro-8-ethyl-5-oxopyrido[2,3-d]pyrimidine-6-carboxylate (compound 42)

To a suspension of ethyl 2-(4-acetyl-1-piperazinyl)-5,8-dihydro-5-oxopyrido[2,3-d]pyrimidine-6-carboxylate (4.0 g), and 6.0 g of potassium carbonate in 100 ml of 50% aqueous ethanol was added with stirring a total of 5.5 ml diethyl sulfate in three portions and the mixture was allowed to react for 2 hours at room temperature.

The reaction product was extracted with chloroform, and the extract dried over anhydrous magnesium sulfate, followed by evaporation of the solvent to leave a crystalline residue, to which n-hexane was added. The crystals were collected and recrystallized from a mixture of n-hexane and acetone to give 3.4 g of the product, m.p. 208° – 210°C with decomposition.

EXAMPLE 27

2-(4-Acetyl-1-piperazinyl)-5,8-dihydro-8-ethyl-5-oxopyrido[2,3-d]pyrimidine-6-carboxylic acid (compound 10)

To a solution of 0.45 g of 2-(4-acetyl-1-piperazinyl)-5,8-dihydro-5-oxopyrido[2,3-d]pyrimidine-6-carboxylic acid in 30 ml of sodium carbonate was added two 0.5 ml portions of diethyl sulfate with stirring at room temperature. After the completion of the reaction the mixture was neutralized with acetic acid. The precipitate resulted was collected and recrystallized from dimthylformamide to yield 0.4 g of the product, m.p. 298° – 300°C.

EXAMPLE 28

2-(1-piperazinyl)- and 2-(4-ethyl-1-piperazinyl)-5,8-dihydro-8-ethyl-5-oxopyrido[2,3-d]pyrimidine-6-carboxylic acids (compound 1 and 21)

To a solution of 1.5 g of 5,8-dihydro-2-(1-piperazinyl)-5-oxopyrido[2,3-d]pyrimidine-6-carboxylic acid in 60 ml of a 10% aqueous solution of sodium carbonate was added three 10 ml portions of diethyl sulfate. After completion of the reaction, the resulting mixture was neutralized with acetic acid. The precipitate was collected and recrystallized from dimethylformamide to give 0.8 g of 2-(1-piperazinyl)-5,8-dihydro-8-ethyl-5-oxopyrido[2,3-d]pyrimidine-6-carboxylic acid (compound 1) m.p. 253° – 255°C. Concentration of the mother liquor to about a half volume gave another solid which was further recrystallized from the same solvent to give 0.6 g of 2-(4-ethyl-1-piperazinyl)-5,8-dihydro-8-ethyl-5-oxopyrido[2,3-d]pyrimidine-6-carboxylic acid (compound 21), m.p. 228° – 230°C.

EXAMPLE 29

5,8-Dihydro-8-ethyl-2-(4-methyl-1-piperazinyl)-5-oxopyrido[2,3-d]pyrimidine-6-carboxylic acid (compound 3)

To a mixture containing 1.0 g of 5,8-dihydro-2-(4-methyl-1-piperazinyl)-5-oxopyrido[2,3-d]pyrimidine-6-carboxylic acid, 1.0 g of 65% sodium hydride, and 40 ml of dimethylformamide held at 60°C, was added 1.0 ml of ethyl iodide. The resulting mixture was heated in a steam bath for 2.5 hours. Dimethylformamide was distilled off in vacuo, the residue dissolved in 10 ml of water, and the resulting solution neutralized with acetic acid. The precipitate was collected and recrystallized from ethanol to yield 0.72 g of the product, m.p. 232° – 233°C.

EXAMPLE 30

Ethyl 2-(4-benzyl-1-piperazinyl)-5,8-dihydro-8-ethyl-5-oxopyrido[2,3-d]pyrimidine-6-carboxylate (compound 55)

A mixture of 1.3 g of ethyl 2-(4-benzyl-1-piperazinyl)-5,8-dihydro-5-oxopyrido[2,3-d]pyrimidine-6-carboxylate, 5.0 ml of ethyl iodide, 20 ml of a 12% aqueous solution of sodium carbonate, and 200 ml of dimethylformamide was heated at 95°C for 3 hours. After removal of the solvent and an excess of the reagent by distillation in vacuo, the resulting residue was taken up in chloroform and filtered. The filtrate was concentrated to dryness to leave a solid which was collected and recrystallized from ethanol to give 1.0 g of the product, m.p. 151° – 153°C.

EXAMPLE 31

8-Benzyl-5,8-dihydro-2-(4-methyl-1-piperazinyl)-5-oxopyrido[2,3-d]pyrimidine-6-carboxylic acid (compound 19)

A mixture of 1.0 g of 5,8-dihydro-2-(4-methyl-1-piperazinyl)-5-oxopyrido[2,3-d]pyrimidine-6-carboxylic acid, 0.6 ml of benzyl chloride, 20 ml of a 12% aqueous solution of potassium carbonate, and 150 ml of dimethylformamide was heated at 95°C for 2 hours. After removal of the solvent and an excess of the reagent, the resulting residue was taken up in water and the aqueous solution neutralized with acetic acid. The solid that separated was collected and recrystallized from dimethylformamide to give 0.7 g of the product, m.p. 251° – 255°C.

EXAMPLE 32

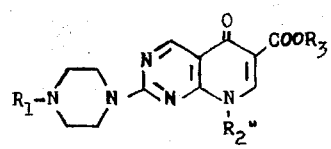

The following compounds were prepared in the same way as in Example 26.

| Compound | $R_1$ | $R_2''$ | $R_3$ | m.p.°C |
|---|---|---|---|---|
| 22 | $CH_3-$ | $C_2H_5-$ | $C_2H_5-$ | 146 – 147° |
| 20 | $C_2H_5OCO-$ | $C_2H_5-$ | H | >300 |

The following compounds were prepared in same way as in Example 27.

| Compound | $R_1$ | $R_2''$ | $R_3$ | m.p.°C |
|---|---|---|---|---|
| 6 | ⟨phenyl⟩- | $C_2H_5-$ | H | 247 – 248 |

The following compounds were prepared in the same way as in Example 28.

| Compound | $R_1$ | $R_2''$ | $R_3$ | m.p.°C |
|---|---|---|---|---|
| 3 | $CH_3-$ | $C_2H_5-$ | H | 232 – 234 |
| 56 | H | $C_2H_5-$ | $C_2H_5-$ | 156 – 158 |

The following compounds were prepared in the same way as Example 29.

| Compound | $R_1$ | $R_2''$ | $R_3$ | m.p.°C |
|---|---|---|---|---|
| 7 | ⟨phenyl⟩-$CH_2-$ | $C_2H_5-$ | H | 204 – 206 |
| 17 | $CH_3O-$⟨phenyl⟩-$CH_2-$ | $C_2H_5-$ | H | 198 – 199 |
| 21 | $C_2H_5$ | $C_2H_5-$ | H | 228 – 230 |
| 39 | $CH_3O-$, $CH_3O-$⟨phenyl⟩-$CH_2-$, $CH_3O-$ | $C_2H_5$ | H | 218 – 220 |
| 38 | $CH≡CCH_2-$ | $C_2H_5-$ | H | 254 – 257 |

The following compounds were prepared in the same way as in Example 30.

| Compound | $R_1$ | $R_2''$ | $R_3$ | m.p.°C |
|---|---|---|---|---|
| 58 | ⟨phenyl⟩-$CH_2-$ | $-C_2H_5-$ | $n-C_3H_7-$ | 156.5 – 158.5 |

EXAMPLE 33

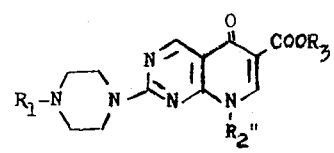

The following compounds were prepared in the same way as in Example 31.

| Compound No. | $R_1$ | $R_2''$ | $R_3$ | m.p.°C | Alkylating agent |
|---|---|---|---|---|---|
| 26 | $CH_3-$ | $n-C_3H_7-$ | H | 254 – 257 | $n-C_3H_7Br$ |
| 31 | $CH_3-$ | $HOCH_2CH_2-$ | H | 232.5 – 233.5 | $HCCH_2CH_2Cl$ |
| 37 | $CH_3-$ | $CH_2=CHCH_2-$ | H | 256 – 258 | $CH_2=CHCH_2Br$ |
| 45 | $CH_3-$ | $ClCH_2CH_2-$ | H | 226 – 228 | $ClCH_2CH_2Cl$ |

EXAMPLE 34

Ethyl 5,8-dihydro-8-(2-hydroxyethyl)-2-(4-methyl-1-piperazinyl)-5-oxopyrido[2,3-d]pyrimidine-6-carboxylate (compound 68)

A mixture containing 5.0 g of ethyl 5,8-dihydro-2-(4-methyl-1-piperazinyl)-5-oxopyrido[2,3-d]pyrimidine-6-carboxylate, 70 ml of dimethylformamide, 0.90 g of 50% sodium hydride, and 3.8 g of ethylene chlorohydrin was heated at 100°C for one hour. Dimethylformamide was distilled off in vacuo, and the residue taken up in chloroform. The chloroform solution was washed with water, dried over anhydrous magnesium sulfate, and the solvent distilled off. The resulting solid was recrystallized from ethanol to yield 4.6 g of the product, m.p. 197° – 199°C.

EXAMPLE 35

Ethyl 8-(2-chloroethyl)-5,8-dihydro-2-(4-methyl-1-piperazinyl)-5-oxopyrido[2,3-d]pyrimidine-6-carboxylate (compound 69)

To a solution of 8.0 g of ethyl 5,8-dihydro-8-(2-hydroxyethyl)-2-(4-methyl-1-piperazinyl)-5-oxopyrido[2,3-d]pyrimidine-6-carboxylate in 80 ml of chloroform was added with stirring 6 ml of thionyl chloride, the resulting mixture was allowed to react at room temperature for 30 minutes and then heated to refux for 2 hours. After removal of the solvent and an excess of the reagent, the residue was taken up in chloroform. The chloroform solution was washed with water, dried and the solvent distilled off. The solid obtained was recrystallized from ethyl acetate to give 6.9 g of the product, m.p. 154° – 155°C.

Examples 36 to 42 illustrate the preparation of the compounds of this invention by the process 4).

EXAMPLE 36

Ethyl 5,8-dihydro-8-ethyl-2-(4-methyl-1-piperazinyl)-5-oxopyrido[2,3-d]pyrimidine-6-carboxylate (compound 22)

A mixture containing 1.0 g of ethyl 5-ethoxy-2-(4-methyl-1-piperazinyl)pyrido[2,3-d]pyrimidine-6-carboxylate and 5.0 ml of dimethylene glycol dimethyl ether was heated to reflux for 3 hours. The solvent was removed by distillation is vacuo and the residual solid was recrystallized from water to yield 0.72 g of the product, m.p. 146° – 147°C.

The starting materials used above were prepared as follows:

Ethyl 5-chloro-2-(4-methyl-1-piperazinyl)-pyrido[2,3-d]pyrimidine-6-carboxylate.

A mixture containing 30 g of diethyl N-[2-(4-methyl-1-piperazinyl)-4-pyrimidinyl]aminomethylene malonate and 150 ml of phosphorous oxychloride was heated at 95°C for 5 hours. An excess of the reagent was removed in vacuo, the residue was made alkaline with 28% aqueous ammonia. The resulting mixture was extracted with chloroform, the extract washed with cold water, and dried over anhydrous magnesium sulfate. The solvent was distilled off to leave a solid which was recrystallized from acetone. There was obtained 23.5 g of the above product as yellow needles, m.p. 173° – 175°C.

Ethyl 5-ethoxy-2-(4-methyl-1-piperazinyl)-pyrido[2,3-d]pyrimidine-6-carboxylate.

A mixture containing 3.0 g of ethyl 5-chloro-2-(4-methyl-1-piperazinyl)pyrido[2,3-d]pyrimidine-6-carboxylate, 0.7 g of sodium ethoxide, and 50 ml of absolute ethanol was heated to reflux for 2 hours. The ethanol was removed by distillation in vacuo, the residue was extracted with chloroform and the extract washed with water, and dried over anhydrous magnesium sulfate. After the solvent was distilled off the residue was crystallized from n-hexane to give 2.8 g of the product as pale yellow needles, m.p. 105° – 108°C.

EXAMPLE 37

Ethyl 5,8-dihydro-8-ethyl-2-(4-methyl-1-piperazinyl)-5-oxopyrido[2,3-d]pyrimidine-6-carboxylate (compound 22)

A mixture containing 1.0 g of ethyl 5-ethoxy-2-(4-methyl-1-piperazinyl)pyrido[2,3-d]pyrimidine-6-carboxylate and 5.0 ml of ethyl iodide was heated to reflux for one hour. After ethyl iodide was recovered by distillation, the resulting solid was crystallized from water to give 0.69 g of the product, m.p. 146° – 147°C.

EXAMPLE 38

Ethyl 5,8-dihydro-8-ethyl-2-(1-piperazinyl)-5-oxopyrido[2,3-d]pyrimidine-6-carboxylate (compound 56)

Following the procedure described in Example 36 using ethyl 5-ethoxy-2-(1-piperazinyl)pyrido[2,3-d]pyrimidine- 6-carboxylate, there is obtained the product, m.p. 156° – 158°C.

EXAMPLE 39

Ethyl 2-(4-acetyl-1-piperazinyl)-5,8-dihydro-8-ethyl-5-oxopyrido[2,3-d]pyrimidine-6-carboxylate (compound 42)

Following the procedure described in Example 37 using ethyl 2-(4-acetyl-1-piperazinyl)-5-ethoxypyrido[2,3-d]pyrimidine-6-carboxylate with ethyl iodide, there is obtained the product, m.p. 208° – 210°C with decomposition.

EXAMPLE 40

Ethyl 2-(4-benzyl-1-piperazinyl)-5,8-dihydro-8-ethyl-5-oxopyrido[2,3-d]pyrimidine-6-carboxylate (compound 55)

Following the procedure described in Example 37 using ethyl 2-(4-benzyl-1-piperazinyl)-5-ethoxypyrido[2,3-d] pyrimidine-6-carboxylate with ethyl iodide, there is obtained the product, m.p. 151° – 153°C.

EXAMPLE 41

Ethyl 2-(4-acetyl-1-piperazinyl)-8-(2-chloroethyl)-5,8-dihydro-5-oxopyrido[2,3-d]pyrimidine-6-carboxylate (compound 61)

A solution of 1.0 g of ethyl 2-(4-acetyl-1-piperazinyl)-5-ethoxypyrido[2,3-d]pyrimidine-6-carboxylate in 10 ml of 1,2-dichloroethane was heated to reflux for 15 hours. After removal of an excess of the reagent by distillation, the resulting solid was taken up in chloroform and the chloroform solution washed with water, and dried over anhydrous magnesium sulfate. The solvent was distilled off to leave a solid which was recrystallized from ethyl acetate to give 0.65 g of the product, m.p. 205° – 206°C.

Ethyl 2-(4-acetyl-1-piperazinyl)-8-(2-bromoethyl)-5,8-dihydro-5-oxopyrido[2,3-d]pyrimidine-6-carboxylate (compound 62)

Following the procedure described above and using 1,2-dibromoethane in place of 1,2-dichloroethane, there is obtained the product, m.p. 202° – 204°C.

EXAMPLE 42

Ethyl 5,8-dihydro-8-(2-hydroxyethyl)-2-(4-methyl-1-piperazinyl)-5-oxopyrido[2,3-d]pyrimidine-6-carboxylate (compound 68)

Following the procedure described in Example 37 using ethyl 2-(4-methyl-1-piperazinyl)-5-ethoxypyrido[2,3-d]pyrimidine-6-carboxylate with ethylenebromohydrine, there is obtained the product, m.p. 197 – 199°C.

Examples 43 to 51 illustrate the preparation of the compounds of this invention by the process 5).

EXAMPLE 43

5,8-Dihydro-8-ethyl-2-(1-Piperazinyl)-5-oxopyrido[2,3-d]pyrimidine-6-carboxylic acid (compound 1).

Ethyl 5,8-dihydro-8-ethyl-5-oxo-2-(1-piperazinyl) pyrido[2,3-d]pyrimidine-6-carboxylate (5.0 g) was dissolved in 30 ml of a 7% aqueous solution of sodium hydroxide by heating at 90°C for 20 minutes. After cooling, the resulting solution was neutralized with acetic acid to yield a precipitate which was collected, and recrystallized from dimethylformamide. There is obtained 4.3 g of the product m.p 253° – 255°C.

EXAMPLE 5,8-Dihydro-8-ethyl-2-(4-methyl-1-piperazinyl)-5-oxopyrido[2,3-d]pyrimidine-6-carboxylic acid (compound 3)

n-Propyl 5,8-dihydro-8-ethyl-2-(4-methyl-1-piperazinyl)-5-oxopyrido[2,3-d]pyrimidine-6-carboxylate (4.5 g) was dissolved in 30 ml of a 10% aqueous solution of sodium carbonate by heating at 95°C for 30 minutes.

After being cooled, the resulting solution was neutralized with acetic acid to give a precipitate which was collected and recrystallized from dimethylformamide. There is obtained 3.8 g of the product, m.p. 232° – 233°C.

EXAMPLE 45

8-Benzyl-5,8-dihydro-2-(1-piperazinyl)-5-oxopyrido[2,3-d]pyrimidine-6-carboxylic acid (compound 33)

Ethyl 8-benzyl-5,8-dihydro-2-(1-piperazinyl)-5-oxopyrido[2,3-d]pyrimidine-6-carboxylate (1.5 g) was dissolved in 20 ml of a 12% aqueous solution of sulfuric acid by heating at 90°C for one hour. The resulting solution was filtered to remove a small amount of the insoluble material and the filtrate was neutralized with 28% aqueous ammonia, to separate a solid which was collected, washed with water, and recrystallized from dimethylformamide. There is obtained 1.1 g of the product, m.p. 250° –253°C.

EXAMPLE 46

Using n-propyl ester as a starting material, the following compounds were prepared in the same way as in Example 44.

| Compound | R₁ | R₂ | m.p.°C |
|---|---|---|---|
| 26 | CH₃— | n-C₃H₇ | 254 – 257 |
| 31 | CH₃— | HOCH₂CH₂— | 232.5 – 233.5 |
| 7 | ⟨C₆H₅⟩CH₂— | C₂H₅— | 204 – 206 |

EXAMPLE 47

Usng ethyl ester as a starting material, the following compounds were prepared in the same way as in Example 44.

| Compound | R₁ | R₂ | m.p.°C |
|---|---|---|---|
| 34 | H | HOCH₂CH₂— | 249 – 251 |

-continued

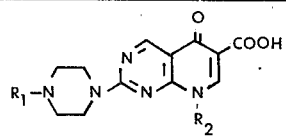

| Compound | R₁ | R₂ | m.p.°C. |
|---|---|---|---|
| 50 | H | CH₂=CHCH₂— | 253 – 255 |
| 37 | CH₃— | CH₂=CHCH₂— | 256 – 258 |
| 18 | HOCH₂CH₂— | C₂H₅— | 226 – 228 |
| 38 | CH≡C—CH₂— | C₂H₅— | 254 – 257 |
| 45 | CH₃— | ClCH₂CH₂— | 226 – 228 |

EXAMPLE 48

Using ethyl ester as a starting material, the following compounds were prepared in the same way as in Example 43.

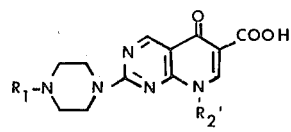

| Compound | R₁ | R₂ | m.p.°C |
|---|---|---|---|
| 2 | H | n-C₃H₇ | 259 – 261 |
| 6 | ⟨phenyl⟩— | C₂H₅— | 247 – 248 |
| 7 | ⟨phenyl⟩-CH₂ | C₂H₅— | 204 – 206 |
| 17 | CH₃O-⟨phenyl⟩-CH₂- | C₂H₅— | 198 – 199 |
| 19 | CH₃— | ⟨phenyl⟩-CH₂- | 251 – 255 |
| 21 | C₂H₅— | C₂H₅— | 228 – 230 |
| 39 | (CH₃O)₃-⟨phenyl⟩-CH₂- | C₂H₅— | 218 – 220 |

EXAMPLE 49

2-(4-Acetyl-1-piperazinyl)-5,8-dihydro-8-ethyl-5-oxopyrido[2,3-d]pyrimidine-6-carboxylic acid (compound 10)

Ethyl 2-(4-acetyl-1-piperazinyl)-5,8-dihydro-8-ethyl-5-oxopyrido[2,3-d]pyrimidine-6-carboxylate (5.0 g) was dissolved in 35 ml of a 10% aqueous solution of sodium carbonate by heating at 90°C for 30 minutes. The resulting solution was filtered to remove the insoluble material, and the filtrate was neutralized with acetic acid to give a precipitate which was collected and recrystallized from a mixture of benzene and chloroform. There is obtained 4.1 g of the product, m.p. 298° – 300°C.

EXAMPLE 50

5,8-Dihydro-2-(4-methyl-1-piperazinyl)-8-vinyl-5-oxopyrido[2,3-d]pyrimidine-6-carboxylic acid (compound 52)

5,8-Dihydro-2-(4-methyl-1-piperazinyl)-8-vinyl-5-oxopyrido[2,3-d]pyrimidine-6-carboxylic acid, m.p. 233° – 234°C, is obtained by hydrolysis of the corresponding ethyl ester as in Example 49.

EXAMPLE 51

5,8-Dihydro-2-(1-piperazinyl)-8-vinyl-5-oxopyrido[2,3-d]pyrimidine-6-carboxylic acid hydrochloride (compound 54)

Ethyl 5,8-dihydro-2-(1-piperazinyl)-8-vinyl-5-oxopyrido[2,3-d]pyrimidine-6-carboxylate (1.0 g) was dissolved in 6 ml of a 10% aqueous solution of sodium carbonate by heating at 95°C. The resulting solution was filtered to remove the insoluble material and acidified with concentrated hydrochloric acid below pH 1. The resulting precipitate was collected and recrystallized from diluted aqueous ethanol to yield 0.78 g of the product, m.p. 298° –301°C with decomposition.

Examples 52 to 53 illustrate the preparation of the compounds of this invention by the process 6.

EXAMPLE 52

5,8-Dihydro-8-ethyl-2-(1-piperazinyl)-5-oxopyrido[2,3-d]pyrimidine-6-carboxylic acid (compound 1)

A. 2-(4-Acetyl-1-piperazinyl)-5,8-dihydro-8-ethyl-5-oxopyrido[2,3-d]pyrimidine-6-carboxylic acid (2.0 g) was dissolved in 40 ml of a 10% aqueous solution of sodium hydroxide by heating at 90° – 95°C for 1.5 hours. The resulting solution was treated with decolorizing charcoal and filtered. The filtrate was neutralized with acetic acid to give 1.6 g of the product as a pure state, m.p. 253° – 255°C.

B. Ethyl 2-(4-acetyl-1-piperazinyl)-5,8-dihydro-8-ethyl-5-oxopyrido[2,3-d]pyrimidine-6-carboxylate (1.6 g) was dissolved in 30 ml of a 10% aqueous solution of sodium hydroxide by heating at 90° – 95°C for one hour. Neutralization of the reaction mixture with acetic acid under cooling yielded a crude solid, which was recrystallized from dimethylformamide to give 1.1 g of the product as a pure state.

EXAMPLE 53

5,8-Dihydro-8-ethyl-2-(1-piperazinyl)-5-oxopyrido[2,3-d]pyrimidine-6-carboxylic acid hydrochloride (compound 11)

A mixture containing, 2.0 g of 5,8-dihydro-8-ethyl-2-(4-formyl-1-piperazinyl)-5-oxopyrido[2,3-d]pyrimidine-6-carboxylic acid and 30 ml of 10% aqueous hydrochloric acid was heated at 90° – 95°C for 1 hour. The reaction mixture was concentrated to dryness and addition of ethanol to the residue resulted in the separation of a solid, which was collected and washed with ethanol to yield 1.7 g of the product, m.p. above 300°C.

EXAMPLE 54

5,8-Dihydro-8-ethyl-2-(1-piperazinyl)-5-oxopyrido[2,3-d]pyrimidine-6-carboxylic acid (compound 1) and 8-benzyl-5,8-dihydro-5-oxo-2-(1-piperazinyl)-pyrido[2,3-d]-pyrimidine-6-carboxylic acid (compound 33)

Following the procedure described in Example 52 (A) using 5,8-dihydro-2-(4-ethoxycarbonyl-1-piperazinyl)-8-ethyl-5-oxopyrido[2,3-d]pyrimidine-6-carboxylic acid or 2-(4-acetyl-1-piperazinyl)-8-benzyl-5,8-dihydro-5-oxopyrido [2,3-d]pyrimidine-6-carboxylic acid, there is obtained, respectively, 5,8-dihydro-8-ethyl-2-(1-piperazinyl)-5-oxopyrido[2,3-d]pyrimidine-6-carboxylic acid, m.p. 253° – 255°C or 8-benzyl-5,8-dihydro-2-(7-piperazinyl)-5-oxopyridio[2,3-d]pyrimidine-6-carboxylic acid, m.p. 250° – 253°C.

EXAMPLE 5,8-Dihydro-8-n-propyl-2-(1-piperazinyl)-5-oxopyrido[2,3-d]pyrimidine-6-carboxylic acid hydrochloride (compound 28) and the corresponding free carboxylic acid (compound 2)

Following the procedure described in Example 53 using 2-(4-acetyl-1-piperazinyl)-5,8-dihydro-8-n-propyl-5-oxopyrido[2,3-d]pyrimidine 6-carboxylic acid, there is obtained 5,8-dihydro-8-n-propyl-2-(1-piperazinyl)-5-oxopyrido[2,3-d]pyrimidine-6-carboxylic acid hydrochloride m.p. 294° – 295°C with decomposition.

The above hydrochloride (1.0 g) was dissolved in 5 ml of water and neutralized with a 5% aqueous solution of sodium bicarbonate to yield the corresponding free carboxylic acid m.p. 259° – 261°C.

EXAMPLE 56

Ethyl 5,8-dihydro-8-ethyl-2-(1-piperazinyl)-5-oxopyrido[2,3-d]pyrimidine-6-carboxylate (compound 56)

A. A mixture containing 4.5 g of ethyl 5,8-dihydro-8-ethyl-2-(4-trifluoroacetyl-1-piperazinyl)-5-oxopyrido[2,3-d]pyrimidine-6-carboxylate, 20 ml of a 7% aqueous solution of potassium carbonates, 50 ml of methanol, and 15 ml of chloroform was allowed to react at room temperature for 1.5 hours with stirring. The solvent was then removed by distillation in vacuo, and the resulting residue was taken up in chloroform. The chloroform solution was dried over anyhydrous magnesium sulfate, and the solvent was distilled off to yield a crude product, which was recrystallized from acetone to give 2.9 g of the product m.p. 156° – 158°C.

B. A solution of 3.0 g of ethyl 2-(4-benzyl-1-piperazinyl)-5,8-dihydro-8-ethyl-5-oxopyrido[2,3-d]-pyrimidine-6-carboxylate in 100 ml of ethanol was allowed to consume an equivalent amount of hydrogen over 1.5 g of 10% palladium-on-carbon under hydrogen atmosphere. The reaction mixture was filtered to remove the catalyst, and the filtrate was concentrated to give a solid which was collected and recrystallized from acetone. There is obtained 2.5 g of the product, m.p. 156° – 158°C.

EXAMPLE 57 n-Propyl 5,8-dihydro-8-ethyl-2-(1-piperazinyl)-5-oxopyrido[2,3-d]pyrimidine-6-carboxylate (compound 57).

Following the procedure described in Example 56 (B), n-Propyl 2-(4-benzyl-1-piperazinyl)-5,8-dihydro-8-ethyl-5-oxopyrido[2,3-d]pyrimidine-6-carboxylate is hydrogenolyzed to yield the product, m.p. 152° –    °C.

EXAMPLE 58

8-(2-chloroethyl)-5,8-dihydro-2-(1-piperazinyl)-5-oxopyrido[2,3-d]pyrimidine-6-carboxylic acid hydrochloride (compound 63)

A mixture containing 1.0 g of ethyl 2-(4-acetyl-1-piperazinyl)-8-(2-chloroethyl)-5,8-dihydro-5-oxopyrido[2,3-d]-pyrimidine-6-carboxylate and 12 ml of 20% aqueous hydrochloric acid was heated on a steam bath for 2 hours, during which period crystals separated out. The crystals were collected, after cooling, and recrystallized from diluted aqueous ethanol containing a small amount of concentrated hydrochloric acid to yield 0.9 g of the product, m.p. 280°C with decomposition.

Examples 59 to 61 illustrate the preparation of the compounds of this invention by the process 7.

EXAMPLE 59

5,8-Dihydro-2-(4-methyl-1-piperazinyl)-8-vinyl-5-oxopyrido[2,3-d]pyrimidine-6-carboxylic acid (compound 52)

A. To a mixture, containing 60 ml of absolute ethanol and 0.65 g of 65% sodium hydride, which was held at 60°C was added with stirring 1.5 g of ethyl 8-(2-chloroethyl)-5,8-dihydro-2-(4-methyl-1-piperazinyl)-5-oxopyrido[2,3-d]pyrimidine-6-carboxylate. The resulting mixture was heated to reflux for one hour and then 30 ml of water added to it. The mixture was refluxed for an additional 30 minutes. The ethanol was distilled off under reduced pressure. The resulting residue was neutralized with 1 N-hydrochloric acid and extracted with chloroform. The extract was washed with water and dried over anhydrous magnesium sulfate. The solvent distilled off. The solid that obtained was recrystallized from a mixture of chloroform and ethanol to give 0.92 g of the product, m.p. 233° – 234°C.

B. A solution of 8-(2-chloroethyl)-5,8-dihydro-2-(4-methyl-1-piperazinyl)-5-oxopyrido[2,3-d]pyrimidine-6-carboxylic acid (1.0 g) in 20 ml of a 10% aqueous solution of sodium hydroxide was heated at 95°C for three hours. The reaction mixture was then neutralized with hydrochloric acid under ice-cooling and chilled. The resulting precipitate was collected to give 0.63 g of the product. Recrystallization from a mixture of chloroform and ethanol gave the product as pure state.

EXAMPLE 60

5,8-Dihydro-2-(1-piperazinyl)-8-vinyl-5-oxopyrido[2,3-d]pyrimidine-6-carboxylic acid hydrochloride (compound 54)

To a mixture, containing 400 ml of absolute ethanol and 2.0 g of 65% sodium hydride, which was held at 60°C was added with stirring 5.0 g of ethyl 2-(4-acetyl-1-piperazinyl)-8-(2-chloroethyl)-5,8-dihydro-5oxopyrido[2,3-d]pyrimidine-6-carboxylate. The resulting mixture was heated to reflux for 2 hours and at the end of the period 200 ml of water was added. The mixture was refluxed for an additional 30 minutes. The ethanol was distilled off under reduced pressure and the resulting residue was acidified with concentrated hydrochloric acid to pH 1.0. The resulting precipitate was collected and recrystallized from water to yield 2.8 g of the product, m.p 298° – 301°C with decomposition.

EXAMPLE 61

5,8-Dihydro-2-(4-methyl-1-piperazinyl)-8-vinyl-5-oxopyrido[2,3-d]pyrimidine-6-carboxylic acid (compound 52)

Following the procedure described in Example 59 (A), using ethyl 5,8-dihydro-8-(2-methanesulfonyloxyethyl)-2-(4-methyl-1-piperazinyl)-5-oxopyrido[2,3-d]pyrimidine-6-carboxylate with potassium tert-butoxide in dimethyl sulfoxide as a solvent, there is obtained the product, m.p. 233° – 234°C.

What is claimed is:

1. An antibacterial pharmaceutical composition comprising as an active ingredient a compound present in a pharmaceutically effective amount of the formula

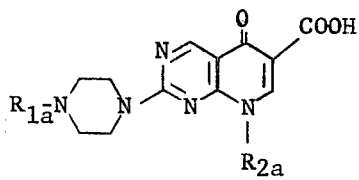

wherein $R_{1a}$ is a moiety selected from one of the group consisting of hydrogen, alkyl having 1 to 4 carbon atoms, hydroxyalkyl having 2 to 4 carbon atoms, phenyl or propargyl, $R_{2a}$ is a moiety selected from one of the group consisting of alkyl having 1 to 4 carbon atoms, alkyl having 2 to 4 carbon atoms substituted by hydroxy or halogen, vinyl, allyl, or benzyl; or pharmaceutically effective organic and inorganic salts thereof, in admixture with a pharmaceutically acceptable adjuvant.

2. An antibacterial pharmaceutical composition comprising as an active ingredient a compound present in a pharmaceutically effective amount of the formula

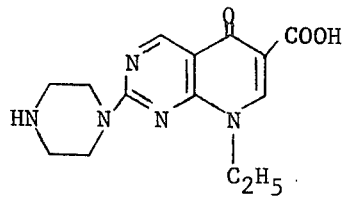

or pharmaceutically effective organic and inorganic salts thereof, in admixture with a pharmaceutically acceptable adjuvant.

3. An antibacterial pharmaceutical composition comprising as an active ingredient a compound present in a pharmaceutically effective amount of the formula

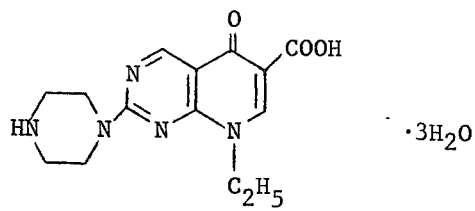

or pharmaceutically effective organic and inorganic salts thereof, in admixture with a pharmaceutically acceptable adjuvant.

* * * * *

UNITED STATES PATENT AND TRADEMARK OFFICE
CERTIFICATE OF CORRECTION

PATENT NO. : 3,962,443
DATED : June 8, 1976
INVENTOR(S) : MINAMI, ET AL.

It is certified that error appears in the above-identified patent and that said Letters Patent are hereby corrected as shown below:

Item 30, line 2, delete "1974", insert -- 1972 --

Signed and Sealed this

Twenty-first Day of September 1976

[SEAL]

Attest:

RUTH C. MASON
Attesting Officer

C. MARSHALL DANN
Commissioner of Patents and Trademarks